(12) United States Patent
Bouton et al.

(10) Patent No.: US 11,224,747 B2
(45) Date of Patent: *Jan. 18, 2022

(54) CLOSED LOOP DEEP BRAIN STIMULATION SYSTEMS AND METHODS

(71) Applicant: Battelle Memorial Institute, Columbus, OH (US)

(72) Inventors: Chad E. Bouton, Columbus, OH (US); Gaurav Sharma, Columbus, OH (US); Bradley C. Glenn, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/708,878

(22) Filed: Dec. 10, 2019

(65) Prior Publication Data
US 2020/0108257 A1 Apr. 9, 2020

Related U.S. Application Data

(63) Continuation of application No. 15/578,783, filed as application No. PCT/US2016/035511 on Jun. 2, 2016, now Pat. No. 10,525,267.
(Continued)

(51) Int. Cl.
*A61B 5/374* (2021.01)
*A61N 1/36* (2006.01)
(Continued)

(52) U.S. Cl.
CPC .......... *A61N 1/36139* (2013.01); *A61B 5/291* (2021.01); *A61B 5/316* (2021.01);
(Continued)

(58) Field of Classification Search
CPC ......... A61B 5/291; A61B 5/316; A61B 5/374; A61B 5/375; A61B 5/4836; A61B 5/6814;
(Continued)

(56) References Cited

U.S. PATENT DOCUMENTS 7,853,329 B2 * 12/2010 DiLorenzo ............. A61B 5/369
607/45
2007/0073355 A1 3/2007 DiLorenzo

FOREIGN PATENT DOCUMENTS

WO WO 2012/088482 A1 6/2012
WO WO 2014/189944 A2 11/2014

OTHER PUBLICATIONS

International Search Report and Written Opinion dated Sep. 1, 2016 in PCT/US2016/035511.

\* cited by examiner

*Primary Examiner* — George Manuel
(74) *Attorney, Agent, or Firm* — Fay Sharpe LLP (57) ABSTRACT

The present disclosure relates generally to systems, methods, and devices for closed loop deep brain stimulation. In particular, a neural signal is measured and provided to software. The software includes a feature generator and a brain network model that takes the neural signal and estimates other neural signals that are not directly measured, and operates as a model of the brain. The software determines a stimulation signal to be sent to stimulating electrodes. Estimated signals by the brain network model are continuously compared to actual signals from the brain. The closed loop feedback system advantageously allows for electrical stimulation levels and patterns to be continuously updated while delivered to a patient.

20 Claims, 3 Drawing Sheets

Related U.S. Application Data (60) Provisional application No. 62/169,835, filed on Jun. 2, 2015.

(51) Int. Cl.
*A61B 5/291* (2021.01)
*A61B 5/316* (2021.01)
*A61B 5/375* (2021.01)
*A61B 5/00* (2006.01)
*A61N 1/05* (2006.01)

(52) U.S. Cl.
CPC .............. *A61B 5/374* (2021.01); *A61B 5/375* (2021.01); *A61B 5/4836* (2013.01); *A61B 5/6814* (2013.01); *A61B 5/6868* (2013.01); *A61B 5/726* (2013.01); *A61B 5/7264* (2013.01); *A61N 1/0534* (2013.01)

(58) Field of Classification Search
CPC ..... A61B 5/6868; A61B 5/726; A61B 5/7264; A61N 1/0534; A61N 1/36139
See application file for complete search history.

CLOSED LOOP DEEP BRAIN STIMULATION SYSTEMS AND METHODS

CROSS-REFERENCE TO RELATED APPLICATIONS

This application is a continuation of U.S. Ser. No. 15/578,783 filed Dec. 1, 2017, which is a 371 national stage entry of PCT Patent Application Serial No. PCT/US2016/035511, filed Jun. 2, 2016, which claims priority to U.S. Provisional Patent Application Ser. No. 62/169,835, filed Jun. 2, 2015, the entirety of which is hereby incorporated by reference.

BACKGROUND

The present disclosure relates generally to systems, methods and devices for closed loop deep brain stimulation. Briefly, a model of the brain is formed in software and is continuously updated by neural signals. The model is used to determine stimulation signals sent to the human brain, and the resulting neural signals are used to provide feedback to the software model of the brain.

Millions of people suffer from neurological disorders such as Parkinson's Disease (PD), epilepsy, essential tremor, dystonia, depression, and obsessive-compulsive disorder. One treatment for these conditions is deep brain stimulation (DBS), wherein a brain pacemaker is implanted into the brain of a patient. The brain pacemaker sends electrical impulses to specific parts of the brain to treat the neurological disorder. DBS can be very effective at managing the symptoms of Parkinson's, which consequently greatly improves the patient's quality of life. DBS may be helpful for certain cases of epilepsy by reducing the frequency and severity of epileptic seizures.

Some commercial brain pacemaker devices have the capability to both electrically stimulate the brain and also sense electrical signals from the brain. However, the devices currently lack working closed loop feedback. Because the devices lack working closed loop feedback, the electrical stimulation delivered by the device must be manually adjusted in repeated office visits. An example of such a device is the Medtronic Brain Radio. It would be desirable to provide fully automatic closed-loop systems that provide feedback (use the output signal as an input) so that effective deep brain stimulation is provided.

BRIEF SUMMARY

The present disclosure relates to systems and methods that can be used to automatically adjust for spatial and/or temporal patterns in a patient's brain during deep brain stimulation. These methods improve the efficacy of the stimulation, maintain that efficacy over time, and may reduce overall power consumption. A closed-loop feedback mechanism is present in a software model of the brain, and permits the system to automatically adjust the electrical stimulation being provided to the patient.

Disclosed herein are methods for adjusting deep brain stimulation, comprising: (a) measuring neural signals in a target area of the brain of a user using sensing electrodes; (b) providing the measured neural signals to a Feature Generator and to a Brain Network Model; (c) using the Brain Network Model to estimate neural signals not directly measurable by the sensing electrodes, and sending the estimated neural signals to the Feature Generator; (d) generating features from the measured neural signals and the estimated neural signals with the Feature Generator, and sending the features to at least one decoder; (e) calculating a feedback index level using output from the at least one decoder; (f) determining an error level between the feedback index level and a desired index level; (g) based on the error level, using a MIMO controller to send a stimulation signal to stimulating electrodes in the target area of the brain; and (h) repeating steps (a)-(g) until the error level between the feedback index level and the desired index level is below a desired value.

The measured neural signals can include single unit action potentials, multi-unit activity, local field potential, signal power across at least one frequency band, and coherence between signals. The sensing electrodes can be implanted or can be placed on the scalp of the user. The sensing electrodes can be placed in the basal ganglia, the motor cortex, the prefrontal cortex, the subthalamic nucleus, the external global pallidus, or the internal global pallidus of the user.

The generated features may include signal amplitude, amplitude of the signal in a given frequency range, amplitude of the signal in a wavelet scale, a firing rate, single unit action potentials, multi-unit activity, local field potential, signal power across at least one frequency band, and coherence between signals.

The methods may further comprise measuring a neurotransmitter level, and sending the measured neurotransmitter level to the at least one decoder. In particular embodiments, the measured neurotransmitter is dopamine, serotonin, or norepinephrine.

The at least one decoder can calculate a condition severity index, an impulsive behavior index, a depressive state index, or an anxiety state index.

The stimulation signal can also be sent to the Brain Network Model. The Brain Network Model may be validated using system identification and optimization techniques. Such system identification and optimization techniques may be selected from the group consisting of regression techniques, genetic algorithms, pattern searches, and Nelder-Mead. In particular embodiments, the at least one decoder has been trained using a condition severity index, a depressive state index, or an anxiety state index determined by a physician.

The methods may further comprise reducing a difference between the measured neural signals and corresponding estimated neural signals by adjusting the Brain Network Model. Thus, future simulations/calculations of the brain state can be more accurate.

Also disclosed are systems for adjusting deep brain stimulation, comprising: (a) sensing electrodes configured to measure neural signals in a target area of a brain of a patient; (b) a Feature Generator which receives the measured neural signals from the sensing electrodes; (c) a Brain Network Model which receives the measured neural signals from the electrodes and estimates neural signals not directly measurable by the sensing electrodes; (d) multiple decoders which receive generated features from the Feature Generator and which calculate a feedback index level; and (e) a MIMO controller which determines an error between the feedback index level and a desired index level and which send a stimulation signal to stimulating electrodes based on the error; wherein the MIMO controller is configured to continually determine a new error between a new feedback index level and the desired index level and send a new stimulation signal to stimulating electrodes based on the new error until the new error is below a desired value.

The DBS systems, methods and devices described herein include closed loop feedback. Desirably, this reduces the number of required visits to a physician for patients using these DBS systems. Other advantages may become apparent to one of ordinary skill in the art upon reading and understanding this disclosure. It is to be understood that a specific embodiment may attain none, one, two, more, or all of these advantages.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the methods and apparatuses disclosed herein can be obtained by reference to the accompanying drawings. These figures are merely schematic representations and are not intended to indicate relative size and dimensions of the assemblies or components thereof.

Although specific terms are used in the following description for the sake of clarity, these terms are intended to refer only to the particular structure of the embodiments selected for illustration in the drawings, and are not intended to limit the scope of the disclosure. In the drawings and the following description below, it is to be understood that like numeric designations refer to components of like function.

The present disclosure relates to systems, methods and devices for providing Deep Brain Stimulation (DBS) that include closed loop feedback. These would be useful for patients who may have neurological disorders such as Parkinson's Disease (PD), epilepsy, essential tremor, Tourette syndrome, and so forth that can be treated using deep brain stimulation. They may also be useful in treating other conditions such as depression, obesity, Alzheimer's disease, chronic pain, and others.

Figure 1:
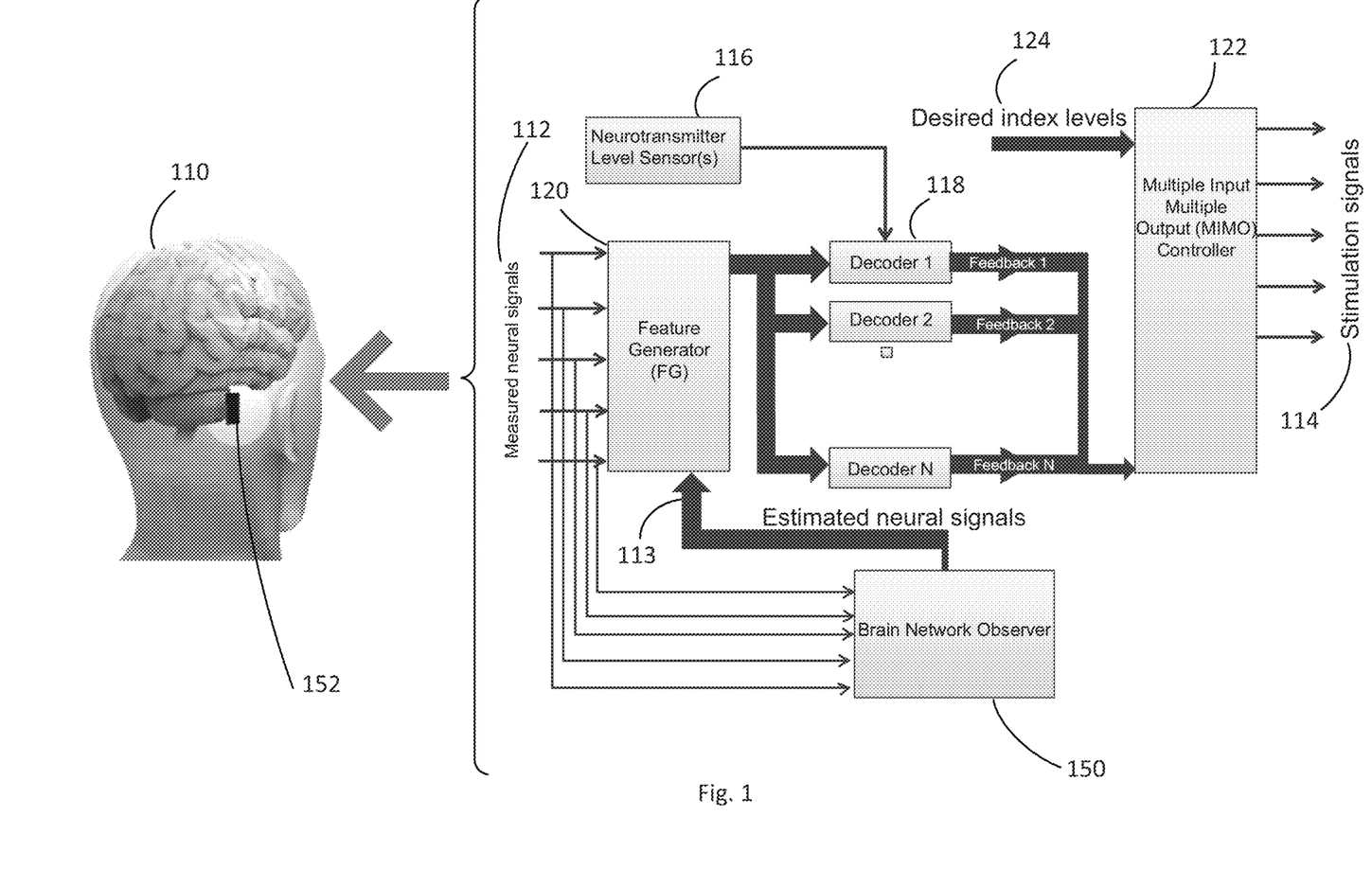
FIG. 1 is a diagram illustrating a Deep Brain Stimulation (DBS) system.

Referring first to FIG. 1, a deep brain stimulation system includes electrodes 152 that are implanted into the brain of a human patient/user/subject 110. The electrodes 152 are used to sense/measure neural signals from the brain, and to deliver electrical pulses as well. This information is sent to a brain pacemaker (not pictured) which sends control/stimulation signals to the electrodes. The brain pacemaker does not need to be implanted inside the head, and is usually implanted subcutaneously below the clavicle or the abdomen. The electrical stimulation pattern sent to the electrodes is determined by a program which can be implemented in hardware or software within the brain pacemaker.

FIG. 1 also illustrates a flowchart/algorithm for measuring a user's neural activity, determining the state of the various neurons in the brain and their electrical patterns, and translating that into an electrical stimulation pattern that can be transmitted to move the electrical patterns of the brain towards a desired state. First, the neural activity of the user/patient is measured to obtain measured neural signals 112 from sensing electrodes. The measured neural signals are sent to both a Feature Generator 120 and to a Brain Network Observer 150. The Brain Network Observer 150 contains a Brain Network Model which is used to estimate neural signals that were not directly measured. Very generally, the Brain Network Model estimates the neural signals that would have been generated by other neurons. These estimated neural signals 113 are also sent to the Feature Generator 120. The Feature Generator 120 then extracts features from the measured neural signals and the estimated neural signals. Subsequently, the extracted feature(s) are sent to decoders 118. In some embodiments, neurotransmitter levels are also measured by sensors in operation 116, and those levels are also sent to the decoders 118. The decoders are used to determine various indices and determine one or more feedback index levels, which is sent to a Multiple Input Multiple Output (MIMO) controller 122. The feedback index level(s) is/are compared to a desired index level(s) 124 to determine one or more error level(s). The MIMO controller then determines the stimulation signal(s) 114 that should be sent to the electrodes to reduce the error levels. The stimulation signal(s) is/are sent to electrodes to stimulate the brain. This algorithm repeats at a high rate, permitting continuous real-time updating of the stimulation signal to the target. Thus, it should be understood that the methods described herein may be performed either continuously or intermittently.

The measured neural signals 112 are measured using sensing electrodes. The same electrodes may be used as both the sensing electrodes and the stimulating electrodes (e.g. such electrodes may alternate between stimulating and sensing). Alternatively, different electrodes may be used for stimulating than are used for sensing. Any suitable electrode array may be used. For example, a "Utah array" of electrodes, such as that made by Blackrock Microsystems, may be used. The Utah array can have up to 96 electrodes. Also contemplated is the use of a "Michigan array" of electrodes, such as that made by NeuroNexus. Custom electrode(s) are also contemplated that may have multiple modalities of recording, stimulation and chemical sensing (through a functional coating) for neurotransmitters. These electrode arrays record "brain waves," more particularly neural signals which are representative of a varied set of mental activities. These neural signals are sent wirelessly or, alternatively, through a wired connection, to a neural signal processing device for processing of the neural signals.

The sensing electrodes may sense electrical signals from different parts of the brain including the basal ganglia (BG) or the motor cortex. Sensing the electrical activity in these parts of the brain is especially useful in treating Parkinson's disease and essential tremor. The BG nuclei include the subthalamic nucleus (STN), the external globus pallidus (GPe), and the internal globus pallidus (GPi), which all play an important role in the pathophysiology of PD and associated network dynamics. The BG acts as a "relay station" for neural activity in the brain, so it may be advantageous to both sense and stimulate in the BG. In addition to the BG, the motor cortex has been found to be an effective area to place the sensing electrodes. This is because the motor cortex is further away from the surface of the brain, and therefore signals received from the motor cortex contain fewer artifacts than signals collected from other areas of the brain. To obtain additional useful information relating to other conditions such as Alzheimer's and obesity, the sensing electrodes may also be located in other areas of the brain such as the prefrontal cortex. It is generally contemplated that the sensing electrodes are implanted in the brain. Alternatively, the sensing electrodes may be placed upon the scalp of the user, for example an electrocorticography (ECoG) or electroencephalography (EEG) electrode array.

The sensing electrodes can measure one or more different neural signals. These neural signals may include single unit action potentials, multi-unit activity, local field potential, signal power across at least one frequency band, and coherence between signals. In additional embodiments, the sensing electrodes or additional sensors also measure the levels of one or more neurotransmitters. The levels of certain neurotransmitters may be particularly useful when treating certain illnesses. For example, monitoring dopamine levels is especially useful in treating PD; and monitoring serotonin, dopamine, or norepinephrine is especially useful in treating depression.

The measured neural signals can then be processed to obtain a "clean" signal. In this regard, for most purposes, it is desirable for each electrode to record the signal from a given neuron, rather than a set of given neurons. The brain is very busy electrically, and the presence of other neurons in the vicinity of these delicate and sensitive electrodes can create noise that obscures the desired signal. The signals actually detected by the electrode array are first amplified and then filtered to remove noise outside of a frequency band of interest (particularly in the range of 0.3 Hz to 7.5 kHz). The signal may be processed in analog or digital form. Examples of useful analog filters include a 0.3 Hz 1st order high pass filter and a 7.5 kHz 3rd order low pass filter. An example of a digital filter is a digital 2.5 kHz 4th order Butterworth low pass filter.

Part of the processing may involve artifact removal. Artifact removal is used to "clean up" the neural activity data and results in improved signals for later use. Artifacts in the data may have been caused by, for example, electrical stimulation of the brain. Identification of an artifact may be accomplished by, for example, by detecting peaks above a threshold crossing in the signal data. The threshold can be fixed or dynamically calculated, and for example can be modified based on factors already known, such as when electrical stimulation is delivered to the brain. A set time window of data may then be removed around the detected artifact. The data is then realigned (e.g. voltage-wise) and then stitched back together (e.g. time-wise). Once such artifacts are removed, the signal is of much smaller magnitude but contains useful information.

Of course, when data is being measured on multiple channels (e.g. from a 96-channel microelectrode array), the artifact should be removed on each channel. One common method of artifact removal is to determine the average from all or most of the channels, and then subtract the average from each channel. Alternatively, the stimulation signal can be shaped in such a way that artifacts on certain frequencies may be prevented or reduced. In other embodiments, the artifacts can be planned somewhat. For example, the electrical stimulation delivered might have a known shape, such as a square pulse. These will aid in identifying and removing artifacts from the neural signals.

As previously mentioned, the measured neural signals are sent to the Feature Generator 120 and the Brain Network Observer 150. Referring still to FIG. 1, the Brain Network Observer 150 is a separate computer module that receives input from the sensing electrodes. The Brain Network Observer includes a Brain Network Model, which acts as a simulated model of the brain and its various neurons, including those which are being measured directly using the sensing electrodes and those neurons which are not being measured directly using the sensing electrodes. In particular, based on the actual neural signals that are measured, the Brain Network Model estimates the neural signals that would be present in neurons not directly measured. The estimated neural signals 113 are the same as those that are measured directly, as listed above. This provides a more "global" view of the brain than would be available without the use of the BNM 150. This global view is advantageous because many illnesses are caused by imbalances in a brain network (e.g. pathways in the brain). These estimated neural signals 113 are also sent to the Feature Generator 120.

Next, the Feature Generator (FG) 120 takes inputs from the measured neural signals 112 and the estimated neural signals 113 and extracts features from them. "Feature" is the term given to various pieces of data, either from each electrode individually or some/all electrodes considered as a group, that can contain useful information for determining the desired movement. Examples of such features include: signal amplitude, amplitude of the signal in a given frequency range, amplitude of the signal in a wavelet scale, or a firing rate. Here, a firing rate may refer to the number of action potentials per unit of time for a single neuron. Other features may include single unit (SU) action potentials, multi-unit activity (MU), local field potential (LFP), signal power (e.g. across a frequency band or bands), and coherence between signals. As used herein, SU relates to electrophysiological responses of a single neuron; LFP relates to an electrophysiological signal generated by the summed electric current flowing from multiple nearby neurons within a small volume of nervous tissue; and MU relates to the activity of several nearby cells when measured simultaneously.

In some applications, a Fast Fourier Transform (FFT) may be used to extract features. Advantageously, an FFT may be used for obtaining power information. Additionally, a nonlinear or linear transform may be use to map the features to N-dimensional space (e.g. by use of a radial basis function). This may be useful when a particular condition can manifest itself in the form of multiple different electrical signals from the electrodes, so that the system can recognize any of those different signals.

The extracted features generated by the Feature Generator 120 are then sent as inputs to individual decoders 118. Each decoder has previously been "trained" to associate certain features with a particular desired feedback. For example, a decoder may have been trained to calculate an index measuring a particular condition, such as a condition severity index. Other feedback index levels created by decoders can include an impulsive behavior index, a depressive state index, or an anxiety state index. The feedback index level calculated by a particular decoder can be a binary output, or can have a range of outputs (e.g. a 1 to 5 scale). It should be noted that a single decoder is also contemplated, although it is generally believed that multiple feedback index levels will be calculated by the algorithm.

Next, the feedback index level(s) are sent to a Multiple Input Multiple Output (MIMO) controller 122. The MIMO controller also receives the desired index level 124 for each feedback index level received from the decoders 118. For example, the decoder may calculate that the current condition severity index has a value of 5, and the desired index level for the condition severity index is a value of 3 or less. The MIMO controller generally calculates an error level between the feedback index level and the desired index level, and then determines an appropriate stimulation signal to the patient's brain that will minimize the error level (i.e. ideally drive the error level to zero) over time. The MIMO controller can use adaptive or nonlinear algorithms as needed to provide robust control signals to the stimulating electrodes.

Figure 2:
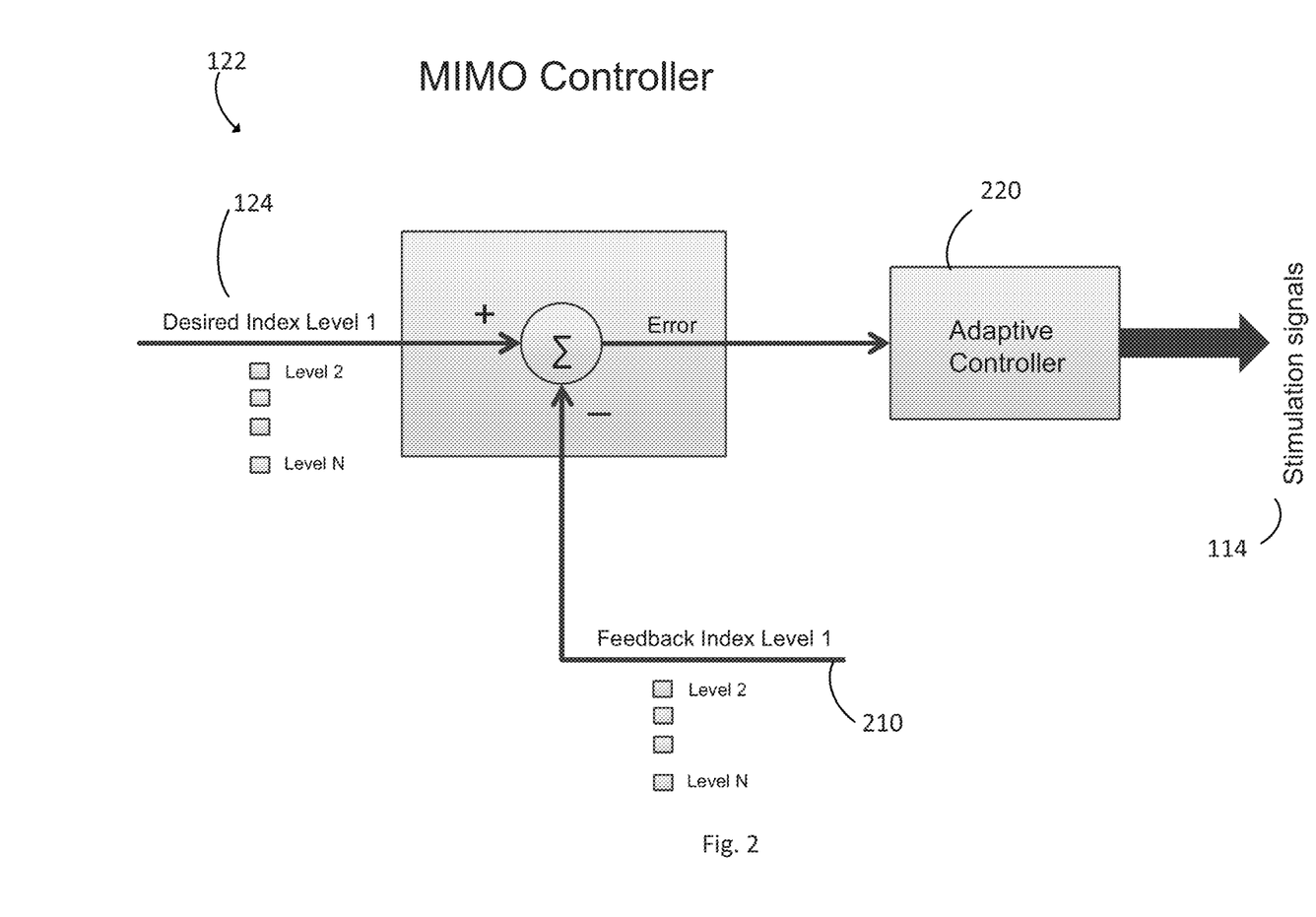
FIG. 2 illustrates the closed loop feedback that is implemented within a multiple input multiple output (MIMO) controller of the present disclosure.

FIG. 2 illustrates the programming of the MIMO controller 122. One or more feedback index levels 210 are received from decoders. These feedback index levels 210 are compared with the desired index levels 124 to generate an error level for each index, which is sent to adaptive controller 220. The adaptive controller 220 then generates the stimulation signals 114, which are sent to the electrodes and stimulate the patient's brain. In some embodiments, the stimulation signals can also be sent to the Brain Network Observer 150 as additional input for calculation and consideration of the estimated neural signals.

The neural signals then measured by the sensing electrodes are sent to the Brain Network Observer, resulting in closed loop feedback to control subsequent stimulation. The present disclosure permits high definition stimulation. In high definition stimulation, the simulation pattern to the stimulating electrodes is "continuously" updated. For example, the stimulation pattern to the electrodes is updated once every 0.1 seconds (e.g. 10 Hz). However, shorter and longer update times are also contemplated; in fact, speeds up to 50 Hz are contemplated. As discussed above, the simulation pattern is provided based on the decoded index levels and is adjusted by the MIMO controller based on the information determined by the Brain Network Observer.

As a result of the deep brain stimulation, desirably the neurological disorder or its symptoms are minimized. The stimulation signal/pattern sent to the electrodes can be changed continuously to obtain the desired result.

Figure 3:
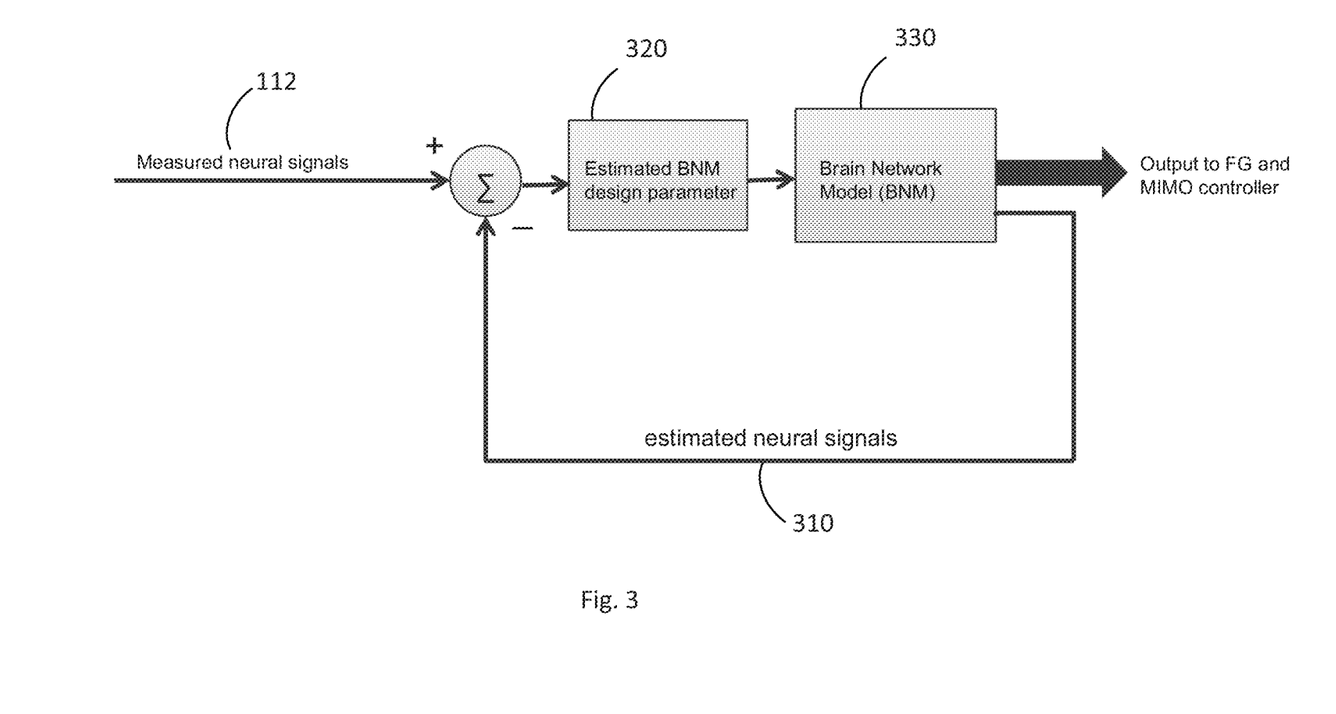
FIG. 3 illustrates an aspect of a brain network model (BNM).

In FIG. 1, the Brain Network Observer 150 receives the measured neural signals 112 and outputs estimated neural signals 113. FIG. 3 illustrates additional details of the operation of the Brain Network Observer 150 module. Again, the Brain Network Model (BNM) 330 is a virtual model of the state of many neurons within the patient's brain, including those that are measured directly and those that are not measured directly. Based on the measured neural signals 112 for directly-measured neurons, the neural signals of non-measured neurons being modeled in the BNM are estimated. The estimation being carried by the BNM also includes estimates of the neural signals for the directly-measured neurons. Those estimated signals 310 can be directly compared to the measured neural signals for those particular neurons, and the difference between the estimated signals and the measured signals can be used to adjust the estimating algorithm 320 of the Brain Network Observer, so that the estimates become more accurate (i.e. the difference is reduced to zero). As the estimates become more accurate, the BNM and its generated output will become more accurate as well.

In order to successfully operate, the algorithms used in the various modules (decoders, Brain Network Observer) must be trained in how to interpret the neural signals that are used as input. The multiple decoders 118 can be trained to output their feedback index level by using data from accelerometers (e.g. for measuring the patient's body tremors) or from a physician's assessment of the patient, imaging information, blood work, and other medical information. For example, in a treatment for depression, an fMRI (functional magnetic resonance imaging) scan may provide an objective, numerical evaluation of the patient's depression which is used to train the decoders. Decoders may be trained by using any test that the physician runs. For example, the condition severity index can be measured by having a physician observe the patient and assign a numerical score. The decoder thus receives information that helps it to identify and assign a feedback level. Certain feedback signals may be related to a particular neurological disorder. For example, a tremor severity/condition severity index may be useful for treating PD; a depressive state index may be useful for treating depression; an anxiety state index may be useful for treating anxiety; and a pain index may be useful for treating chronic pain. Once trained, the decoders will no longer require manual intervention.

The Brain Network Model (BNM) is trained for each individual person, as different people will of course have different neural signals for identical conditions. The BNM itself can be validated using system identification and optimization techniques such as regression, genetic algorithms, pattern search, Nelder-Mead etc. In regression techniques, a mathematical relationship between dependent variables and independent variables is created. For example, using a location of a neural signal and an amplitude of the neural signal, a mathematical relationship may be created which is used to estimate an amplitude of another neural signal at another location. In genetic algorithms, rather than directly creating a mathematical relationship, a population of candidate solutions is "seeded" and then "evolved" through iterations towards an optimum solution. In this regard, genetic algorithms mimic the process of natural selection. For example, a genetic algorithm may start with a population of ten randomly generated brain models. Then, during a first iteration, the genetic algorithm may select the best fit brain model from the population and randomly generate slight variations on that brain model to create a new population of ten brain models. This process may continue to iterate until the selected brain model contains characteristics that are within an acceptable range of desired characteristics. Pattern search, on the other hand, is not an iterative method that converges to a solution. Pattern search refers to a numerical optimization method which has no requirement that any gradient of the problem be optimized. This allows pattern search methods to be used on functions that are not continuous or differentiable. In a Nelder-Mead method, which is a numerical method, the minimum or maximum may be found of an objective function in a many-dimensional space. This relies on the concept of a 'simplex' (a polytope of n+1 vertices in n dimensions). A segment on a line, a triangle on a plane, a tetrahedron in three-dimensional space are all examples of simplexes. The Nelder-Mead method operates by approximating a local optimum of a problem with many variables when an objective function varies smoothly and is unimodal.

The disclosed processing components (e.g. 116, 118, 120, 122 and 150 of FIG. 1) are suitably embodied by an electronic data processing device such as a computer or parallel computing system. Alternatively, they can be embodied in hardware.

It will further be appreciated that the disclosed techniques may be embodied as a non-transitory storage medium storing instructions readable and executable by a computer, (microprocessor or microcontroller of an) embedded system, or various combinations thereof. The non-transitory storage medium may, for example, comprise a hard disk drive, RAID or the like of a computer; an electronic, magnetic, optical, or other memory of an embedded system, or so forth.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method for adjusting deep brain stimulation, comprising:

measuring neural signals in a target area of the brain of a user using sensing electrodes;

generating features from the measured neural signals, and sending the features to at least one decoder;

calculating a feedback index level using output from the at least one decoder;

determining an error level between the feedback index level and a desired index level;

determining a stimulation signal based on the error level and sending the stimulation signal to stimulating electrodes operatively connected to stimulate the brain of the user; and repeating the measuring, the generating of the features, the calculating of the feedback index level, the determining of the error level, and the determining and sending of the stimulation signal to continuously update the stimulation signal sent to the stimulating electrodes.

2. The method of claim 1, wherein the measured neural signals include single unit action potentials, multi-unit activity, local field potential, signal power across at least one frequency band, and coherence between signals.

3. The method of claim 1, wherein the sensing electrodes include electrodes placed on the scalp of the user to measure motor cortex activity.

4. The method of claim 1, wherein the generated features include signal amplitude, amplitude of the signal in a given frequency range, amplitude of the signal in a wavelet scale, a firing rate, single unit action potentials, multi-unit activity, local field potential, signal power across at least one frequency band, and coherence between signals.

5. The method of claim 1, wherein the sensing electrodes include sensing electrodes implanted in the brain and sensing neural signals in the basal ganglia of the user.

6. The method of claim 5, wherein the sensing electrodes implanted in the brain and sensing neural signals in the basal ganglia of the user include sensing electrodes implanted in the brain and sensing neural signals in the subthalamic nucleus.

7. The method of claim 5, wherein the sensing electrodes implanted in the brain and sensing neural signals in the basal ganglia of the user include sensing electrodes implanted in the brain and sensing neural signals in the globus pallidus.

8. The method of claim 1, further comprising measuring a neurotransmitter level, and sending the measured neurotransmitter level to the at least one decoder.

9. The method of claim 8, wherein the neurotransmitter is dopamine, serotonin, or norepinephrine.

10. The method of claim 1, wherein the at least one decoder calculates a condition severity index, an impulsive behavior index, a depressive state index, or an anxiety state index.

11. The method of claim 1, wherein the at least one decoder has been trained using a condition severity index, a depressive state index, or an anxiety state index determined by a physician.

12. A system for adjusting deep brain stimulation, comprising:

sensing electrodes configured to measure neural signals in a target area of a brain of a patient;

a Feature Generator which receives the measured neural signals from the sensing electrodes;

multiple decoders which receive generated features from the Feature Generator and which calculate a feedback index level; and a Multiple Input Multiple Output (MIMO) controller which determines an error between the feedback index level and a desired index level and which send a stimulation signal to stimulating electrodes based on the error;

wherein the MIMO controller is configured to continually determine a new error between a new feedback index level and the desired index level and send a new stimulation signal to stimulating electrodes based on the new error until the new error is below a desired value.

13. The system of claim 12, wherein the sensing electrodes include sensing electrodes implanted in the brain and sensing neural signals in the basal ganglia of the user.

14. The system of claim 13, wherein the sensing electrodes implanted in the brain and sensing neural signals in the basal ganglia of the user include sensing electrodes implanted in the brain and sensing neural signals in the subthalamic nucleus.

15. The system of claim 13, wherein the sensing electrodes implanted in the brain and sensing neural signals in the basal ganglia of the user include sensing electrodes implanted in the brain and sensing neural signals in the globus pallidus.

16. A non-transitory storage medium storing instructions readable and executable by a microprocessor or microcontroller to iteratively perform a deep brain stimulation adjustment method including:

receiving neural signals measured in a target area of the brain of a user using sensing electrodes;

generating features from the neural signals;

calculating feedback index levels for conditions of the user by applying, to the generated features, decoders trained to calculate indices measuring the respective conditions of the user;

determining error levels between the feedback index levels and corresponding desired index levels;

determining a stimulation signal based on the error levels; and sending the stimulation signal to stimulating electrodes operatively connected to stimulate the brain of the user;

wherein the deep brain stimulation adjustment method is performed iteratively to continuously update the stimulation signal sent to the stimulating electrodes.

17. The non-transitory storage medium of claim 16, further including:

receiving measurements of at least one neurotransmitter level;

wherein the calculating of the feedback index levels is by applying, to the generated features and the measurements of the at least one neurotransmitter level, decoders trained to calculate indices measuring the respective conditions of the user.

18. The non-transitory storage medium of claim 17, wherein the at least one neurotransmitter level includes a dopamine level.

19. The non-transitory storage medium of claim 18, wherein the at least one neurotransmitter level further includes a serotonin level and/or a norepinephrine level.

20. The non-transitory storage medium of claim 16, wherein the calculating of feedback index levels for conditions of the user include calculating of feedback index levels for conditions of the user including one or more of an impulsive behavior index, a depressive state index, and/or an anxiety state index.

* * * * *